US009907580B2

(12) United States Patent
Perkins et al.

(10) Patent No.: US 9,907,580 B2
(45) Date of Patent: Mar. 6, 2018

(54) ADJUSTABLE SPINOUS PROCESS SPACER DEVICE AND METHOD OF TREATING SPINAL DISORDERS

(71) Applicant: Bryson Medical Technology LLC, Staatsbury, NY (US)

(72) Inventors: Richard Perkins, Staatsburg, NY (US); Matthew G. Baynham, Jupiter, FL (US)

(73) Assignee: Bryson Medical Technology LLC, Staatsburg, NY (US)

( * ) Notice: Subject to any disclaimer, the term of this patent is extended or adjusted under 35 U.S.C. 154(b) by 0 days.

(21) Appl. No.: 14/857,392

(22) Filed: Sep. 17, 2015

(65) Prior Publication Data

US 2016/0074076 A1    Mar. 17, 2016

Related U.S. Application Data

(63) Continuation-in-part of application No. 13/209,427, filed on Aug. 14, 2011, now abandoned, which is a continuation-in-part of application No. 11/600,321, filed on Nov. 16, 2006, now Pat. No. 7,998,173.

(60) Provisional application No. 60/738,930, filed on Nov. 22, 2005.

(51) Int. Cl.
*A61B 17/70* (2006.01)
*A61B 17/86* (2006.01)

(52) U.S. Cl.
CPC ...... *A61B 17/7068* (2013.01); *A61B 17/7049* (2013.01); *A61B 17/86* (2013.01)

(58) Field of Classification Search
CPC ..................... A61B 17/80–17/8095
See application file for complete search history.

(56) References Cited

U.S. PATENT DOCUMENTS

| | | | |
|---|---|---|---|
| 4,738,251 A | 4/1988 | Plaza | |
| 4,998,936 A | 3/1991 | Mehdian | |
| 5,092,889 A | 3/1992 | Campbell, Jr. | |
| 5,133,716 A | 7/1992 | Plaza | |
| 5,234,431 A * | 8/1993 | Keller | A61B 17/7007 606/287 |
| 5,393,036 A | 2/1995 | Sheridan | |
| 5,496,318 A | 3/1996 | Howland et al. | |
| 5,810,815 A | 9/1998 | Morales | |
| 6,190,387 B1 * | 2/2001 | Zucherman | A61B 17/025 606/249 |
| 6,312,431 B1 * | 11/2001 | Asfora | A61B 17/7068 606/263 |
| 6,364,883 B1 * | 4/2002 | Santilli | A61B 17/7068 606/279 |
| 6,451,019 B1 | 9/2002 | Zucherman et al. | |
| 6,451,020 B1 | 9/2002 | Zucherman et al. | |
| 6,652,527 B2 | 11/2003 | Zucherman et al. | |
| 7,083,621 B2 | 8/2006 | Shaolian et al. | |
| 7,201,751 B2 | 4/2007 | Zucherman et al. | |
| 7,588,591 B2 * | 9/2009 | Hartmann | A61B 17/7062 606/246 |

(Continued)

*Primary Examiner* — Jan Christopher Merene
*Assistant Examiner* — Steven Cotroneo
(74) *Attorney, Agent, or Firm* — McHale & Slavin, P.A.

(57) ABSTRACT

Provided is a bi-dimensionally adjustable spacing device configured to be placed between the spinous processes of at least two adjacent vertebrae and also adjusted laterally to securely contact the lateral surfaces of the spinous process. A method of using the device to treat spinal disorders is also provided.

15 Claims, 25 Drawing Sheets

(56) References Cited

U.S. PATENT DOCUMENTS

| | | | |
|---|---|---|---|
| 7,806,911 B2* | 10/2010 | Peckham | A61B 17/7059 606/248 |
| 7,998,173 B2 | 8/2011 | Perkins | |
| 8,262,697 B2* | 9/2012 | Kirschman | A61B 17/7068 606/248 |
| 8,343,190 B1* | 1/2013 | Mueller | A61B 17/7068 606/248 |
| 2003/0040746 A1* | 2/2003 | Mitchell | A61B 17/1606 623/17.11 |
| 2003/0153915 A1 | 8/2003 | Nekozuka et al. | |
| 2004/0249379 A1* | 12/2004 | Winslow | A61B 17/7062 606/249 |
| 2006/0106381 A1 | 5/2006 | Ferree et al. | |
| 2006/0247640 A1* | 11/2006 | Blackwell | A61B 17/7068 606/71 |
| 2007/0203495 A1 | 8/2007 | Zucherman et al. | |
| 2008/0021466 A1* | 1/2008 | Shadduck | A61B 17/08 606/249 |
| 2008/0033445 A1 | 2/2008 | Zucherman et al. | |
| 2008/0058941 A1 | 3/2008 | Zucherman et al. | |
| 2008/0167655 A1 | 7/2008 | Wang et al. | |
| 2008/0167656 A1 | 7/2008 | Zucherman et al. | |
| 2008/0177271 A1 | 7/2008 | Yeh | |
| 2008/0288075 A1 | 11/2008 | Zucherman et al. | |
| 2008/0306556 A1 | 12/2008 | Zucherman et al. | |
| 2009/0248076 A1 | 10/2009 | Reynolds et al. | |
| 2009/0248079 A1 | 10/2009 | Kwak et al. | |
| 2010/0036419 A1* | 2/2010 | Patel | A61B 17/7065 606/249 |
| 2011/0144692 A1* | 6/2011 | Saladin | A61B 17/7053 606/249 |
| 2013/0296939 A1 | 11/2013 | Perkins | |

* cited by examiner

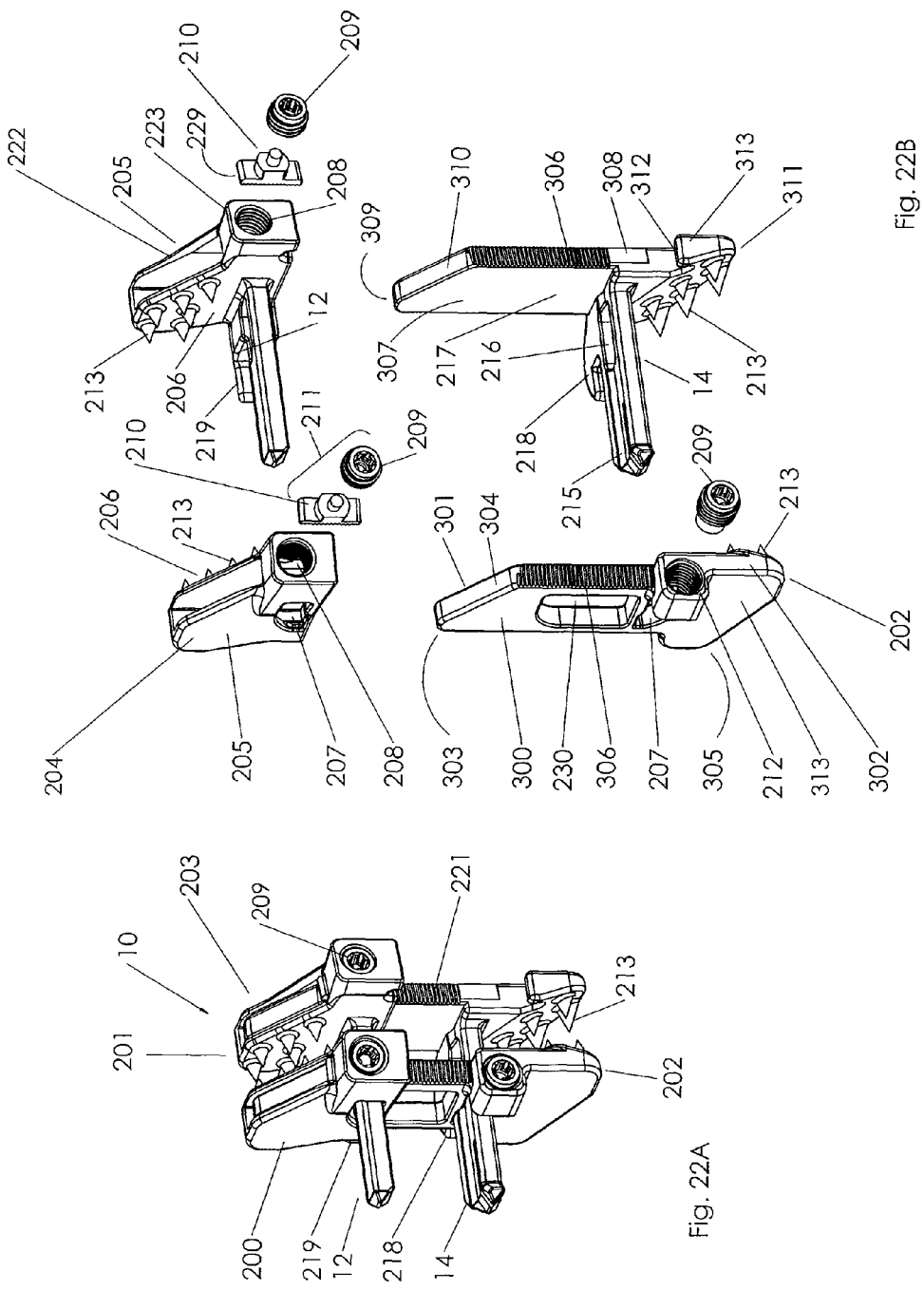

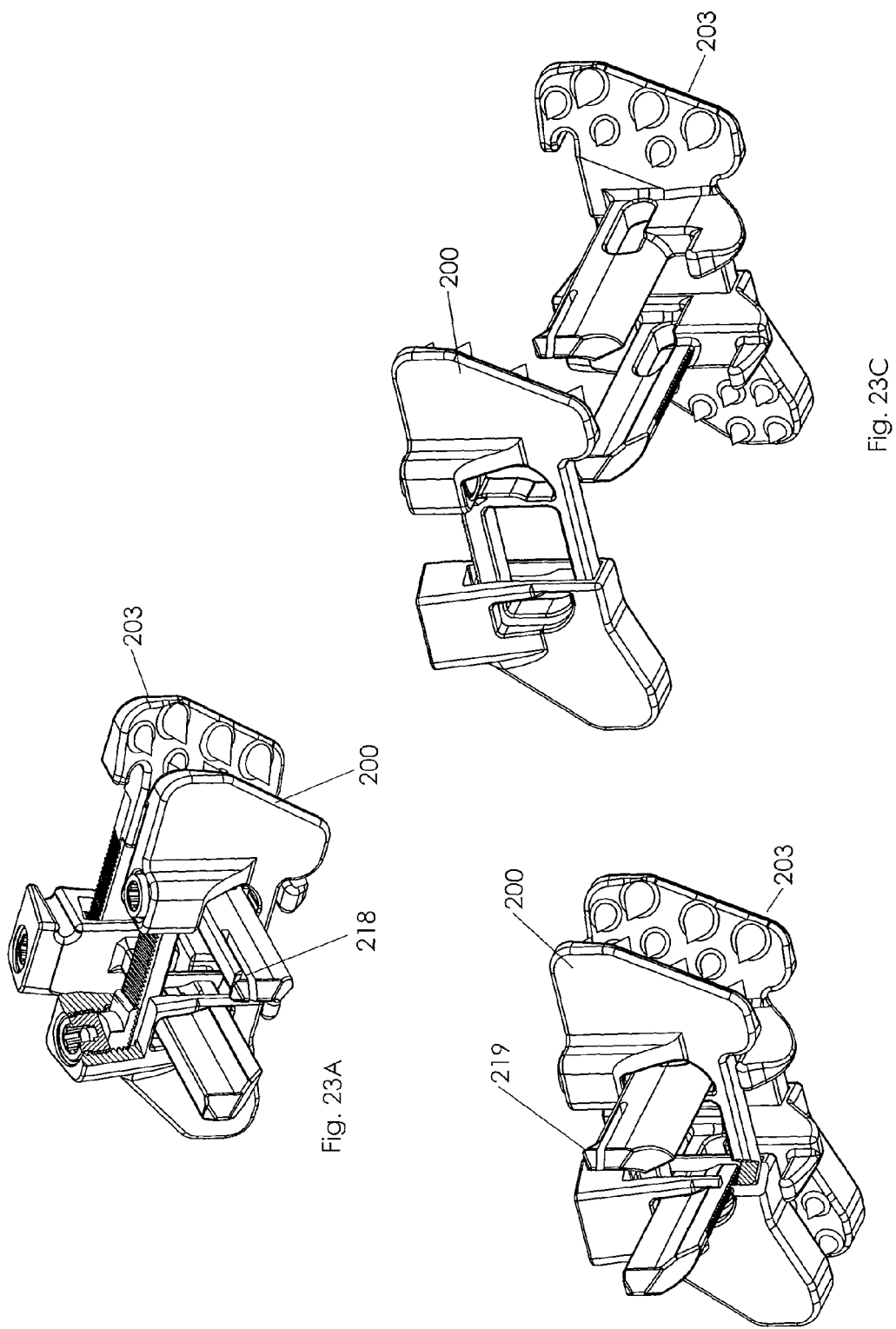

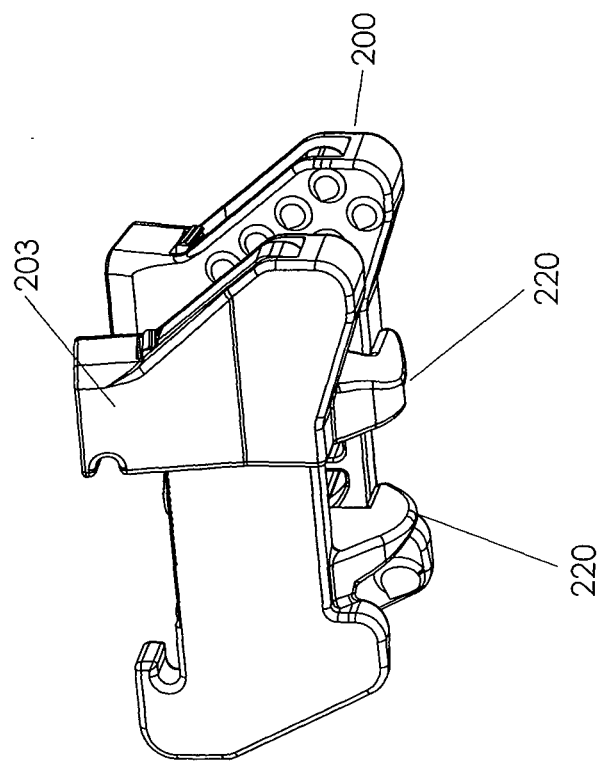
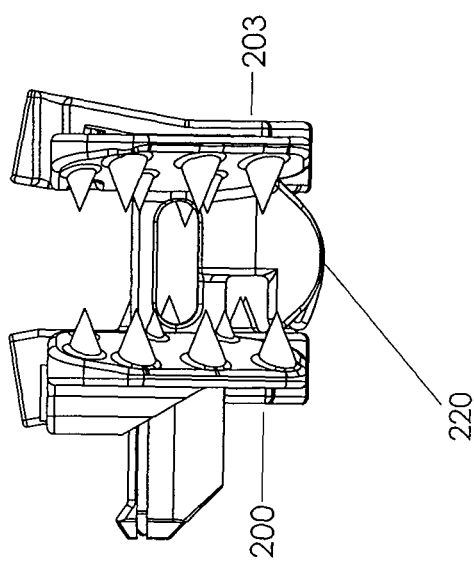
Fig. 24B
Fig. 24A

ADJUSTABLE SPINOUS PROCESS SPACER DEVICE AND METHOD OF TREATING SPINAL DISORDERS

CROSS REFERENCE TO RELATED APPLICATIONS

In accordance with 37 C.F.R. § 1.76, a claim of priority is included in an Application Data Sheet filed concurrently herewith. The present application is a continuation in part application of U.S. patent application Ser. No. 13/209,427, filed Aug. 14, 2011 which is a continuation in part application of patent application Ser. No. 11/600,321, filed Nov. 16, 2006, now U.S. Pat. No. 7,998,173 which claim priority to U.S. Provisional Application No. 60/738,930, filed Nov. 22, 2005, the complete disclosures of which are herein incorporated by reference.

FIELD OF THE INVENTION

The present invention relates to devices and methods for use in spine surgery. In particular, the present invention relates to a bi-dimensionally adjustable spacing device configured to be placed between the spinous processes of at least two adjacent vertebrae and also adjusted laterally to securely contact the lateral surfaces of the spinous process. A method of using the device to treat spinal disorders is also provided.

BACKGROUND

The human spine is comprised of thirty-three vertebrae at birth and twenty-four as a mature adult. Between each pair of vertebrae is an intervertebral disc, which maintains the space between adjacent vertebrae and acts as a cushion under compressive, bending and rotational loads and motions. A healthy intervertebral disc has a great deal of water in the well hydrated nucleus pulposus, the center portion of the disc. The water content gives the nucleus a spongy quality and allows it to absorb spinal stress.

In a young healthy individual, the intervertebral disc also serves as a natural spacer between adjacent vertebrae thus allowing sufficient space in the central spinal canal and intervertebral foramina to permit unimpeded nerve passage3 from the neural canal. In addition to injuries or disease of the intervertebral discs, the common condition of spinal stenosis can impinge upon neural and vascular structures leading to neurological compromise.

Spinal stenosis is a common condition resulting from the narrowing of the spinal canal, nerve root canals and intervertebral foramina causing nerve pinching, which leads to persistent pain, lack of feeling and decreased physical activity. The narrowing of nerve egress pathways from the vertebral column results in compression of spinal nerves and nerve roots, causing a constellation of symptoms, including lower back pain, neurogenic claudication and lower extremity pain.

While spinal stenosis is a pervasive cause of such pain and disability, there are many other spinal conditions, diseases, and injuries among patients of all ages that create a need to provide effective relief for a growing population of spinal disorder patients.

SUMMARY

Disclosed herein is a device that meets the above identified need by providing a novel device and method for the treatment of spinal disorders. More particularly, a device is disclosed that provides a spacer, adjustable on two planes that can be easily positioned between adjacent spinous processes so as to relieve the pressure between adjacent vertebrae as a treatment for spinal disorders.

Disclosed is a device for use in the treatment of spinal disorders that includes an assembly having two approximately parallel elongated legs, the legs being adjustably connected one to the other by transverse members that are adjustable in two planes.

Also disclosed is a device for treating spinal disorder and injuries that includes an assembly having two approximately parallel elongated legs being adjustably connected one to the other by transverse members that are adjustable in two planes with each transverse member having a shape suitable to abut against a respective spinous process of a vertebrae so as to form a device having a box-like configuration abutted against and between at least one pair of adjacent spinous processes of respective adjacent vertebrae.

Also disclosed in as method of treating spinal stenosis that includes providing the device disclosed herein and using surgical methods to position the device on the dorsal side of the spinal column of a patient such that the two legs are positioned one on either side of the center of the spinal column and approximately parallel thereto, positioning the first transverse member against the spinous process of a first vertebra and moving the adjacent adjustable transverse member to a position abutting against the spinous process of a second adjacent vertebra and adjusting the relationship of the transverse member to each of the two legs disposed on each side of the spinous processes, locking the adjustable transverse member into position on the two legs so as to form an adjustably fixed spacer between the first spinous process and the second adjacent spinous process.

Also disclosed herein is a spinal device comprising plates held in an approximately parallel orientation one to the other and positioned between spinous processes of two adjacent vertebrae, spinous pads for longitudinal extensions or adjustments, spacers for lateral extensions and gripping.

Other aspects are described infra.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 1A shows a dorsal view of two adjacent vertebrae having a first exemplary embodiment of the bi-dimensionally adjustable spinous process spacer device inserted between and abutted against adjacent spinous processes with the first and second elongated, longitudinal legs positioned away from each other and not in contact with the spinous process located there between.

FIG. 1B shows a dorsal view of two adjacent vertebrae having a first exemplary embodiment of the bi-dimensionally adjustable spinous process spacer device inserted between and abutted against adjacent spinous processes with the first and second elongated, longitudinal legs positioned toward each other and in contact with the spinous process located there between.

FIGS. 22A, 22B show an assembled device (FIG. 22A) and a disassembled device (FIG. 22B) of the seventh exemplary embodiment.

FIGS. 23A-23C show views from different viewing angles of the device.

FIGS. 24A, 24B show a top view providing an illustration of the anchoring structures (FIG. 24A) and the U-shaped hook-like protrusion for slidably engaging the outer side of the through portals of the first longitudinal member (FIG. 24B).

FIG. 25A shows a side loading initial positioning. FIG. 25B shows a top loading initial positioning. FIG. 25C shows a vertical lock-up lateral expanded intermediate position. FIG. 25D shows a vertical lock-up lateral lock-up final position.

DETAILED DESCRIPTION

Detailed embodiments of the present invention are disclosed herein; however, it is understood that the following description and each of the accompanying figures are provided as being exemplary of the invention, which may be embodied in various forms without departing from the scope of the claimed invention. Thus, the specific structural and functional details provided in the following description are non-limiting, but serve merely as a basis for the invention as defined by the claims provided herewith. The device described below can be modified as needed to conform to further development and improvement of materials without departing from the inventor's concept of the invention as claimed.

The device and components thereof, as generally shown at 10 in FIG. 1 through FIG. 21, is a novel bi-dimensionally adjustable spinous process spacer device capable of securely maintaining a selected distance between the spinous processes of two or more adjacent vertebrae and also allowing for lateral positioning of elements of the device 10 so as to make secure contact with the lateral surfaces of the spinous process of the vertebrae to which the device is attached.

As demonstrated in the discussions of each of the exemplary embodiments of the device 10, the general concept of providing a device 10 that is capable of being adjusted relative to the spinal vertebrae on two planes and securely locked into place is constant with the only variations being the selected mechanism for accomplishing the function of the inventive concept.

Figure 1A:
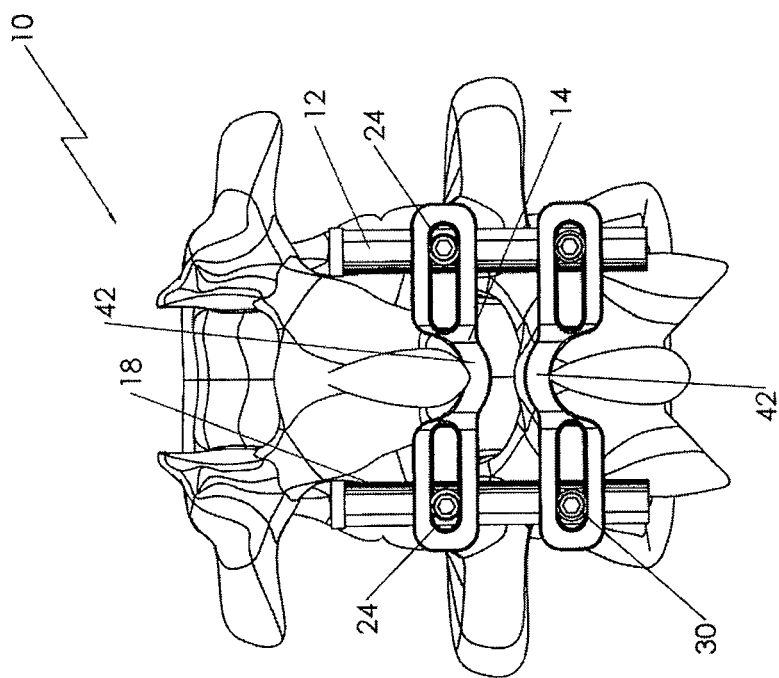

As shown in the first exemplary embodiment of the bi-dimensionally adjustable spinous process spacer device, shown in FIG. 1A through FIG. 4, two relatively parallel longitudinal members 12 can be positioned along the longitudinal axis of the spine and on either side of the spinous processes of the underlying vertebrae. Transverse members 14 can be provided having oblong through portals 16 sized and configured to allow passage of the elongated longitudinal legs 12. The oblong through portals 16 permit longitudinally directed movement of the transverse members 14 relative to the spinous process of adjacent vertebrae and relative to other transverse members 14. Additionally, the oblong through portals 16 allow the elongated legs 12 to be adjusted laterally so as to bring the transverse members into a position in contact with the lateral surface of the spinous process. FIGS. 1A and 1B best demonstrate this lateral positioning of the elongated legs 12 and the transverse members 14 relative to the spinous process of the vertebra. As shown in FIG. 1A, the elongated legs are extended within the oblong through portals 16 laterally, away from the spinous process of the vertebra. As shown in FIG. 1B, the elongated legs 12 have been laterally adjusted inward within the oblong through portals 16 so as to bring the elongated legs 12 into contact with the lateral surface of the spinous process. Surface contact structures 18, which can be in the form of a textured surface, ribs, spikes, or any other frictional contact augmenting structures can also be provided on the surface of the elongated legs 12 for the purpose of improving secure contact between the elongated legs 12 and the lateral surface of the spinous process.

Figure 1B:
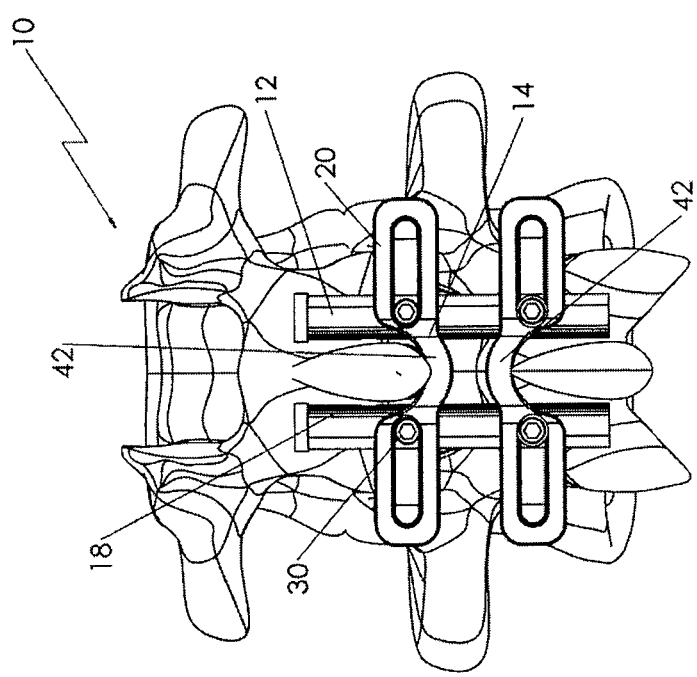
Figure 2:
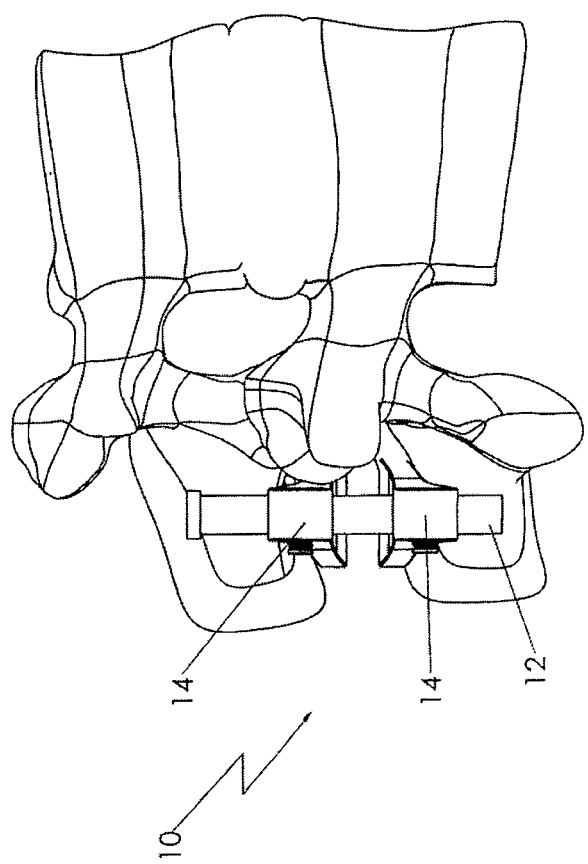
FIG. 2 shows a side view of a first and a second adjacent vertebra having a first exemplary embodiment of the bi dimensionally adjustable spinous process spacer device inserted between the two adjacent spinous processes, the device having a caudally inclining transverse member abutted against the first spinous process and a cephalid inclining transverse member abutted against the second spinous process so as to hold the two adjacent vertebra in a fixed spatial relationship one to the other. Also shown are gradation indicia on the surface of the longitudinal legs.
Figure 3:
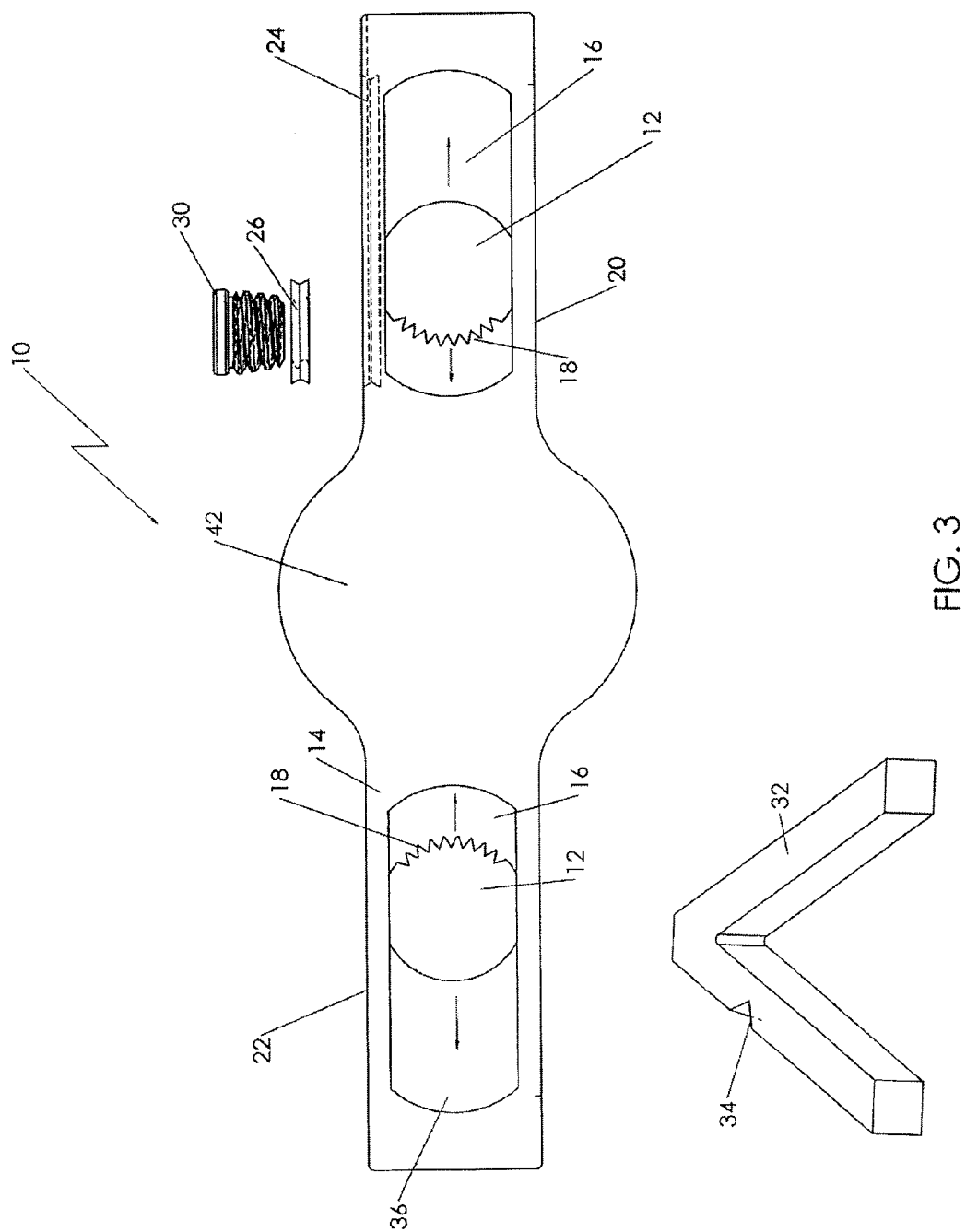
FIG. 3 shows a front view of a transverse member of a first exemplary embodiment of the bi-dimensionally adjustable spinous process spacer device. On a first end of the transverse member is shown an exemplary locking device for the elongated, longitudinal legs, which as seen from the end are positioned within their respective oblong through portals in the transverse member, the first exemplary locking device, which is shown on the right includes a threaded grommet having an expansion cut, the grommet being slidably engaged within an elongated locking portal and a set screw capable of threadably engaging the threaded slidable grommet so as to laterally expand the expansion cut of the grommet pressing the grommet against the walls of the elongated locking portal to lock its relative position within the locking portal and to securely engage and hold in position the elongated, longitudinal leg. A second exemplary locking device is shown in a pre-insertion position on the left side of the depiction of a transverse member, the exemplary locking device being an outwardly biased insertable clip having a locking notch to engage and exert an outward holding pressure against the elongated legs within the oblong through portal defined in the transverse member.
Figure 4:
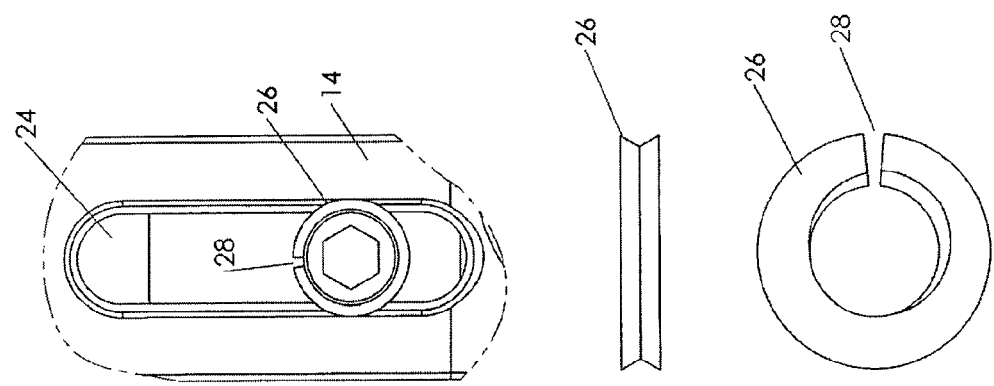
FIG. 4 shows a detail of the threaded slidable grommet of the first exemplary embodiment shown in FIG. 3 positioned within the elongated locking portal defined in the upper portion of the end of the transverse member.

As shown in FIGS. 1A, 1B, and FIG. 3, this first exemplary embodiment of the device 10, can be secured into a selected configuration longitudinally relative to the spinous processes of adjacent vertebra and laterally relative to the lateral surfaces of the spinous processes by more than one locking system. Two exemplary locking devices for the first described embodiment of the device 10 are shown in FIG. 3. These non-limiting examples of locking devices demonstrate a wide variance in locking devices that can be adapted to this embodiment of the device 10. As shown on the right side 20, the upper surface of the lateral extensions of the transverse member 14 can define an elongated locking portal 24 located directly over the oblong through portal 16 through which the elongated legs 12 pass. The oblong through portal 16 can be provided with a threaded grommet 26 configured to be slidably engaged and adjustably held within the through portal 16. Provision of an expansion cut 28 facilitates inward compression of the threaded grommet for assembly within the through portal 16. The provision of the expansion cut 28 is also advantageous when a locking screw 30 is threaded into the threaded grommet 26 and due to the oversized dimension of the locking screw 30 effects an outward expansion of the threaded grommet 26 thus locking the screw 30, the threaded grommet 26 and the longitudinal leg 12 into a secure, locked position relative to each other and the vertebra and the spinous process.

An alternative locking device to secure the longitudinal legs into a fixed position within the oblong through portals in the transverse members 14 is shown on the left side 22 of the transverse member 12 shown in FIG. 3 in a pre-insertion position relative to the transverse member 14. The exemplary locking device as shown is an outwardly biased insertable clip 32 having a locking notch 34 to engage and exert an outward holding pressure against the elongated legs within the oblong through portal defined in the transverse member. When the clip 32 is fully inserted, the locking notch 34 engages the outer edge 36 of the oblong through portal 16 and securely holds the elongated leg 12 in its selected position relative to the transverse member 14 and the spinous process of the adjacent vertebra.

Figure 5:
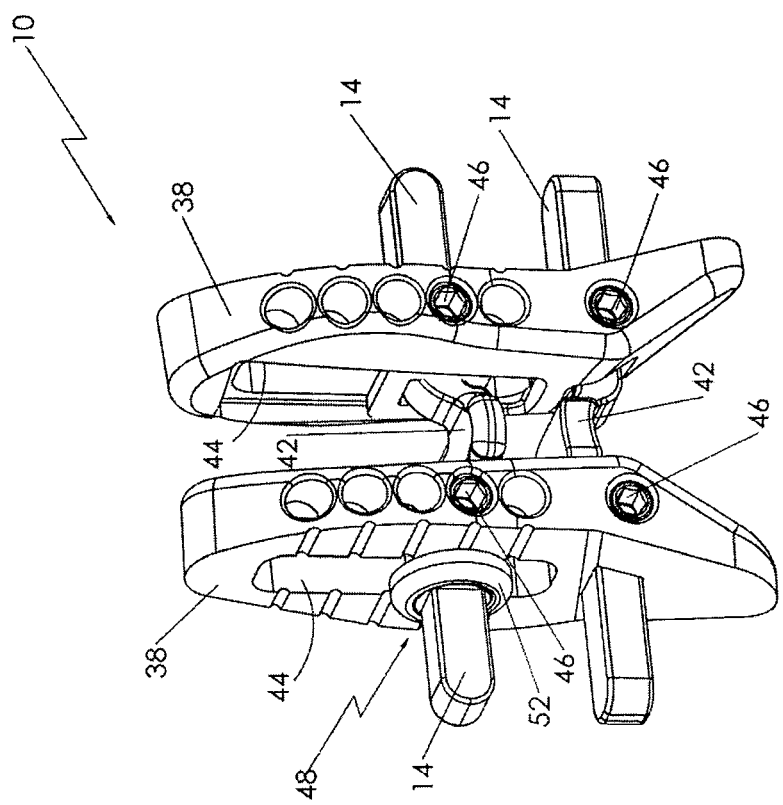
FIG. 5 shows a frontal perspective view of a second exemplary embodiment of the bi-dimensionally adjustable spinous process spacer device, the embodiment employing a collet locking device to secure the device in the lateral plane when positioned on either side of a spinous process of a vertebra and a set screw locking device for securing the device between two adjacent vertebra and holding the adjacent spinous process in a fixed relationship one to the other.
Figure 6:
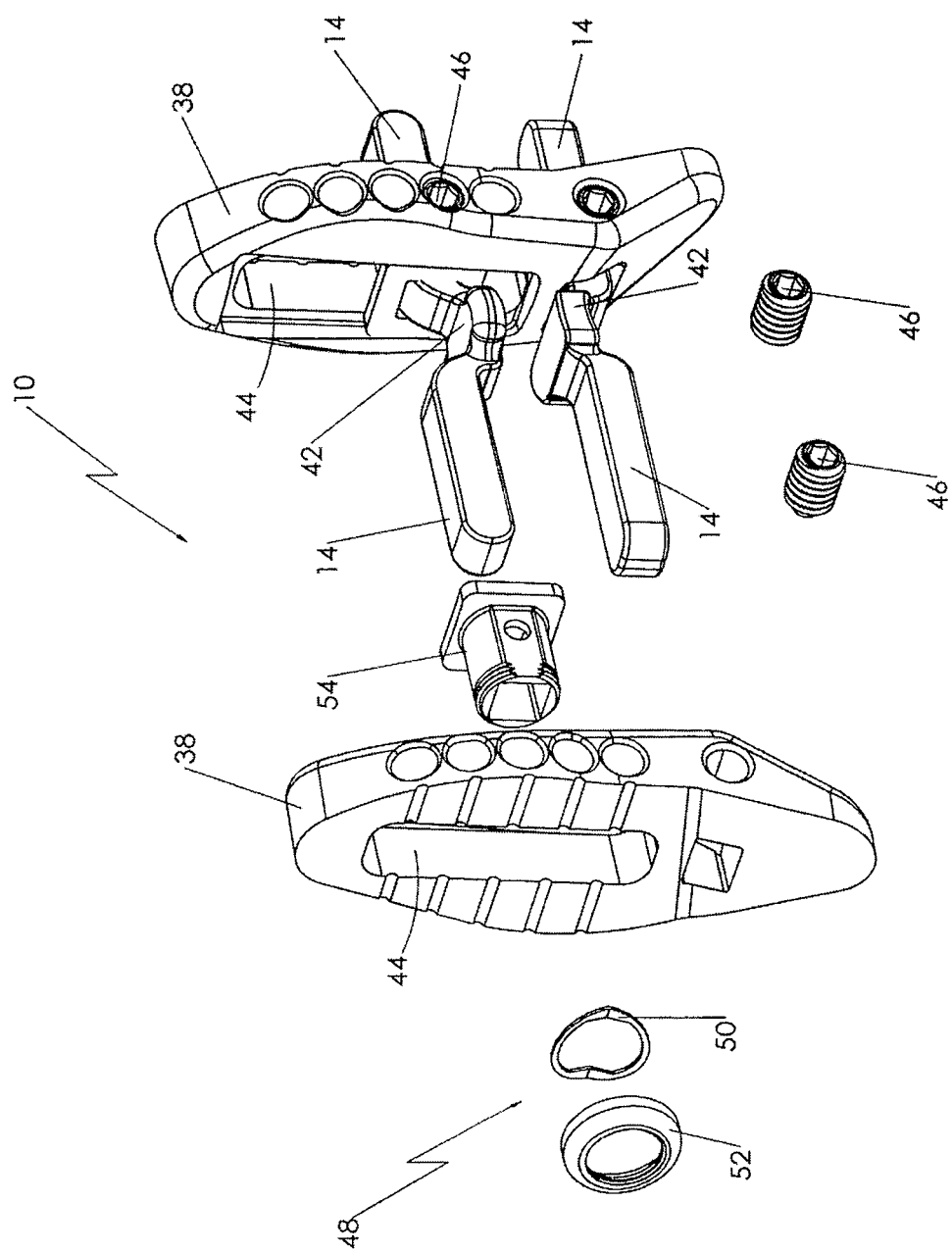
FIG. 6 shows an exploded view of the second exemplary embodiment of the bi-dimensionally adjustable spinous process spacer device of FIG. 6 having a collet lock.
Figure 7:
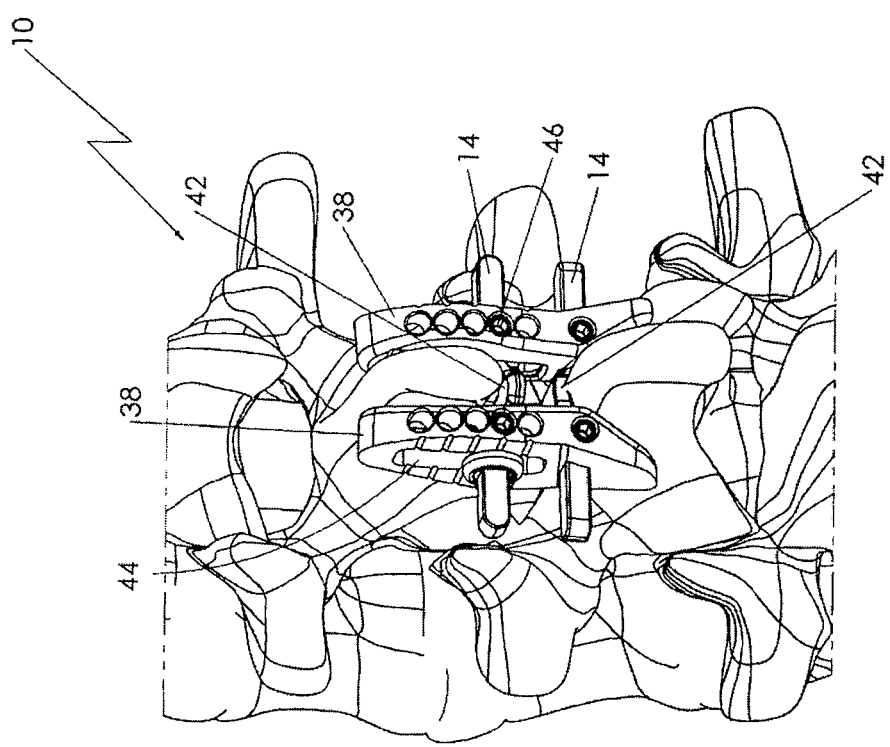
FIG. 7 shows the second embodiment of the bi-dimensionally adjustable spinous process spacer device of FIG. 6 having a collet lock in position between two adjacent vertebrae, holding the two adjacent spinous processes in a fixed spatial relationship one to the other and having the device securely abutted against the lateral surfaces of the spinous process.
Figure 8:
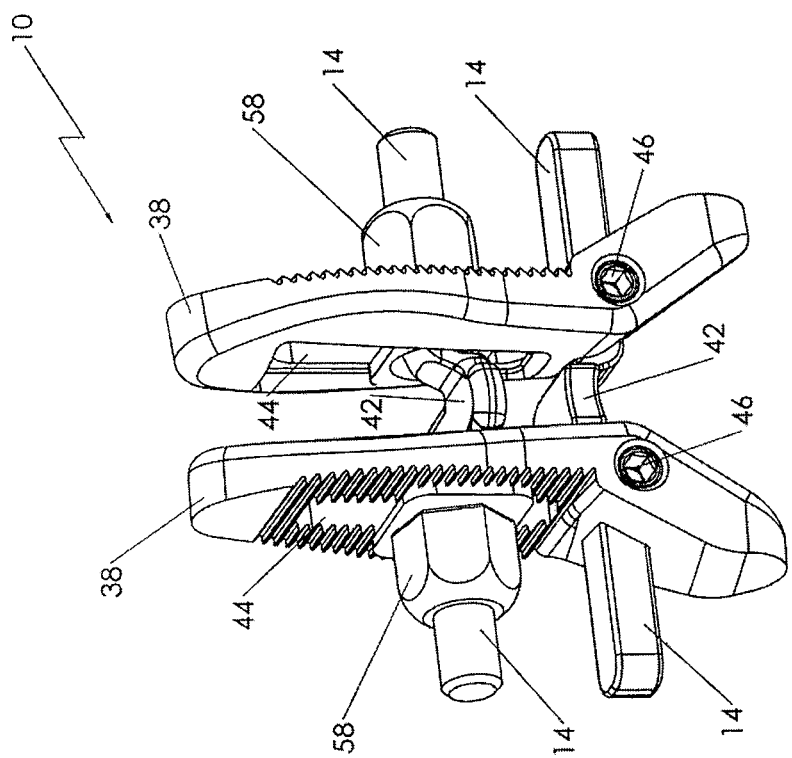
FIG. 8 shows a frontal perspective view of a third exemplary embodiment of the bi-dimensionally adjustable spinous process spacer device having a fitted lateral ratchet locking device to secure the device between two adjacent vertebra and holding the adjacent spinous process in a fixed spatial relationship one to the other while employing set screws to secure the device in a selected position on either side of the spinous process of a vertebra.

A second exemplary embodiment of the device 10 as shown in FIGS. 5-7 is, as other embodiments, capable of being adjusted longitudinally so as to set and hold the relative position of two adjacent spinous processes while also permitting adjustment of the transverse members relative to the elongated legs 12 so as to bring the outlying elongated legs into a secure contact position against the lateral surfaces of the spinous process. As shown in FIGS. 5-7, rather than providing elongated legs as shown in the first exemplary embodiment, are instead provided in a broader side plate 38 configuration wherein the transverse members 14 pass through transverse member adjustment slots 44 defined through the side plates 38. The transverse members 14, as in other embodiments are provided with ergonomically configured caudal or cephalid directed central sloping areas to better conform to the shape of the spinous processes with which the central portion 42 of the transverse member 14 makes contact. As shown in FIGS. 5-7 the adjustment of the transverse members 14 upward or downward along the longitudinal axis of the side plates 38 is accomplished by adjustment of the transverse member end portions within the elongated transverse member adjustment slots 44 defined laterally through the body of the side plates 38. When the transverse members 14 are selectively adjusted to the desired location within the adjustment slots 44, their relative positions can be securely locked using a set locking set screw 46. Additionally, a collet lock mechanism, generally shown at 48 can be provided as shown in FIGS. 5-7. the tension member 50, the locking cap 52, and the transverse member guide 54 each being configured to permit the lateral end of the transverse member to pass through serve to guide the transverse member upward or downward within the transverse member adjustment slots 44 and exert a holding tension on the end portions of the transverse member 14 keeping it in a secure track position within the side plates 38.

Figure 9:
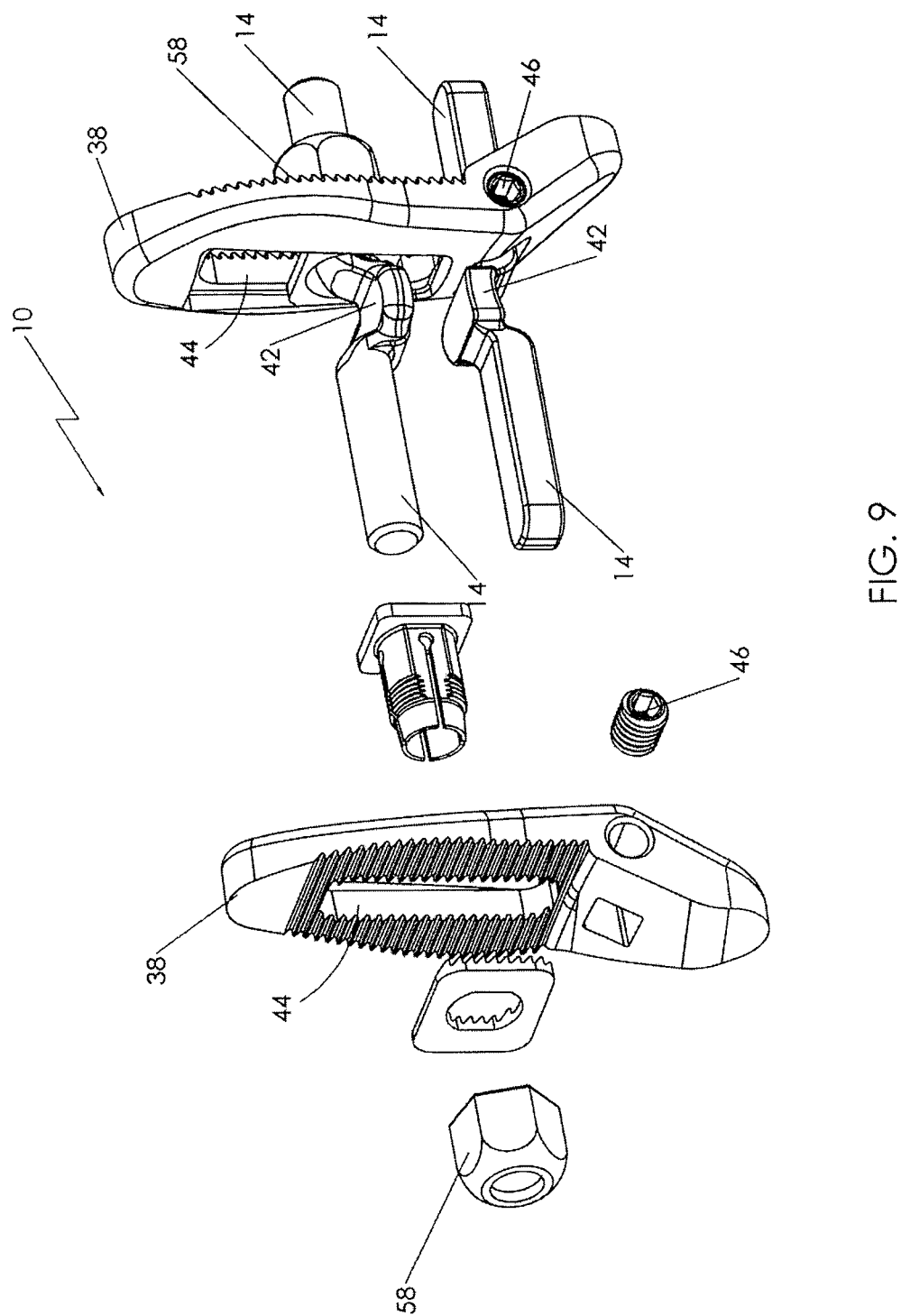
FIG. 9 shows an exploded view of the third exemplary embodiment of the bi-dimensionally adjustable spinous process spacer device of FIG. 6 having a fitted lateral ratchet locking device.
Figure 10:
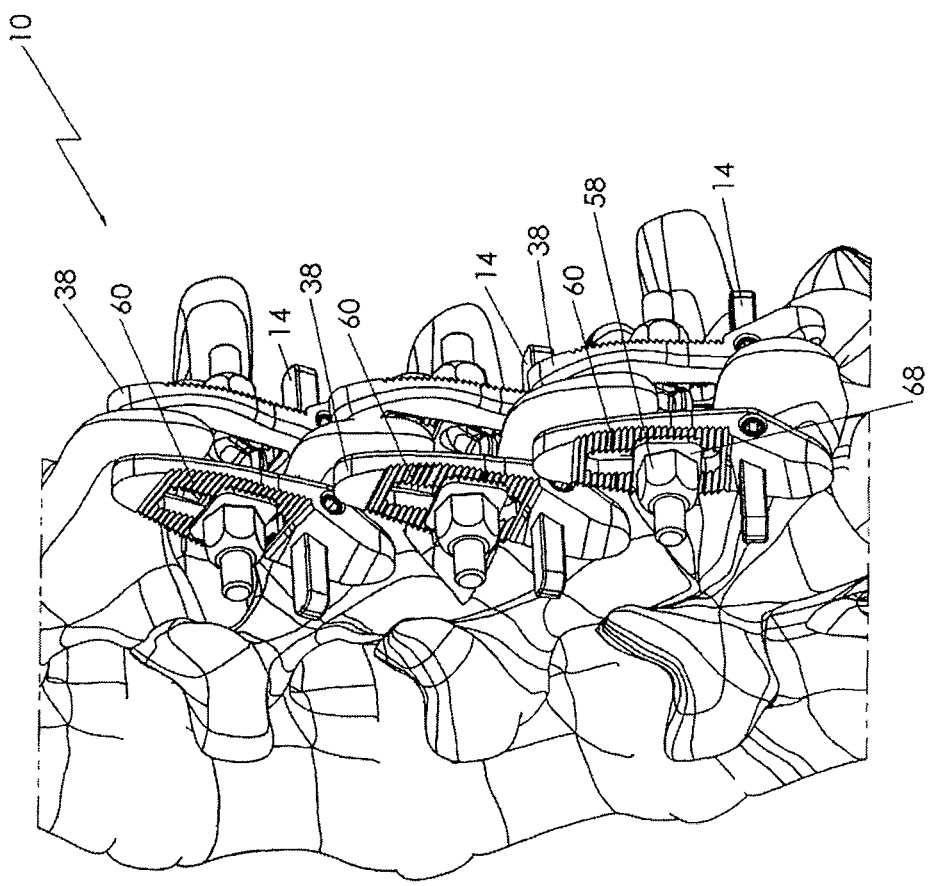
FIG. 10 shows three devices of the third exemplary embodiment of the bi-dimensionally adjustable spinous process spacer device of FIG. 6 having a fitted lateral ratchet locking device in position between adjacent vertebrae, holding the adjacent spinous processes in a fixed spatial relationship one to the other and having the device securely abutted against the lateral surfaces of the respective spinous processes.

A third exemplary embodiment of the device 10 as shown in FIGS. 8-11 is, in similar fashion to the second exemplary embodiment described above, capable of being adjusted longitudinally so as to set and hold the relative position of two adjacent spinous processes while also permitting adjustment of the transverse members 14 relative to the side plates 38 so as to bring the outlying side plates 38 inward into a secure contact position against the lateral surfaces of the spinous process. In this third exemplary embodiment of the device 10, the transverse members 14 pass through transverse member adjustment slots 44 defined through the side plates 38. Other elements of the device 10, such as the caudal or cephalid directed central sloping areas of the transverse members 14 are also similar to those already described for other embodiments. As shown in FIGS. 8-11 the adjustment of the transverse members 14 upward or downward along the longitudinal axis of the side plates 38 is accomplished by adjustment of the transverse member end portions within the elongated transverse member adjustment slots 44 defined laterally through the body of the side plates 38. As best shown in FIG. 9 when the transverse members 14 are selectively adjusted to the desired location within the adjustment slots 44, their relative positions can be securely locked using the compressive force of a collet-like guide sleeve 40 having circumferentially disposed compression slots 56 that when the threaded end nut 58 is locked down secures the transverse member 14 into position. Additionally, a locking screw can be used to secure the transverse member from unwanted lateral movement. The outward facing lateral surfaces of the side plates 38 can be provided with a ratchet surface 60 or a similar contact surface configuration to support holding the side plates 38 in a locked position relative to the transverse member 14. A complementary opposing ratchet surface 62 can be provided on the locking plate 64.

Figure 11:
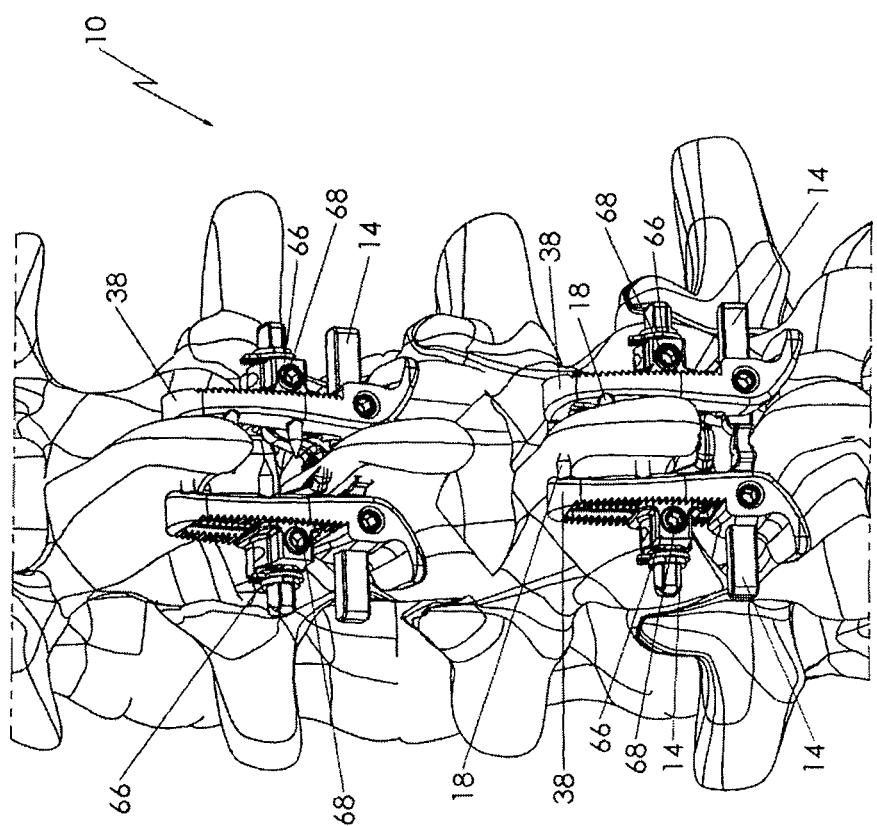
FIG. 11 shows an alternative configuration of the fitted lateral ratchet embodiment shown in FIGS. 8-10 of the bi-dimensionally adjustable spinous process spacer device using a set screw for securing the fitted ratchet in place relative to the transverse member. Also shown is the device having multiple spike contacts to augment the security of the device against the lateral surface of the spinous process.

FIG. 11 shows a variation of the third exemplary embodiment of the device 10 as described above in that instead of a threaded end nut 58 as described above, the transverse member 14 is locked into a selected position through the use of a transverse member locking block 66 through which the transverse member 14 passes. A block set screw 68 is used to secure the position of the transverse member 14 within the locking block 66. As shown in FIG. 11, this variation of the third exemplary embodiment also includes the use of surface contact structures such as spikes 18 to facilitate a secure hold on the lateral surfaces of the spinous process.

Figure 12:
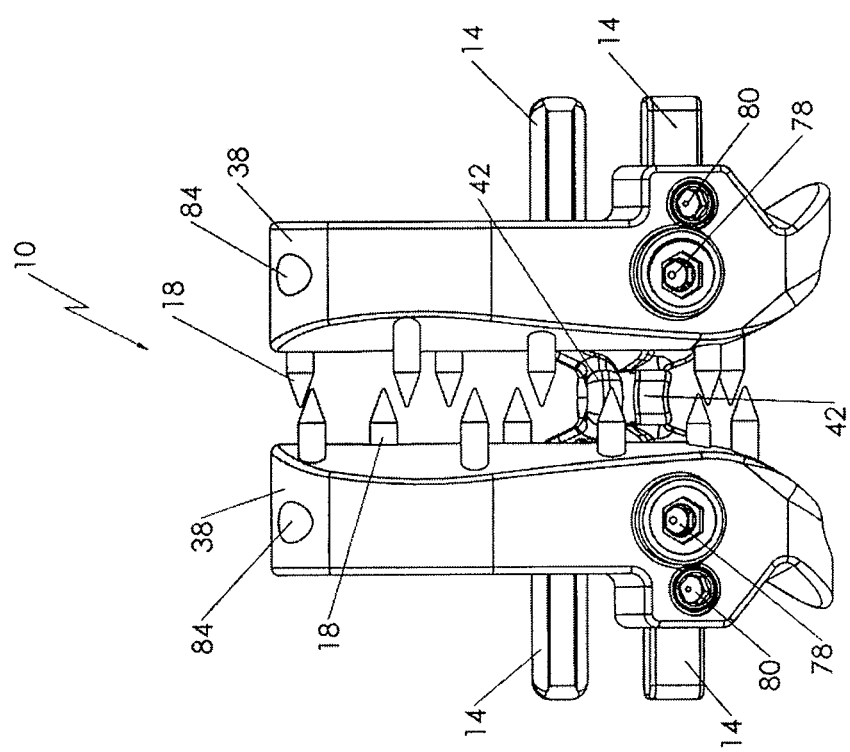
FIG. 12 shows a frontal view of a fourth exemplary embodiment of the bi-dimensionally adjustable spinous process spacer device having a rotating gear mechanism for adjusting the distance between transverse members positioned between the spinous processes of adjacent vertebra. Also shown is the set screw locking device for securing the lateral position plates equipped with spike fixation augmentation members against the lateral surfaces of the spinous process.
Figure 13:
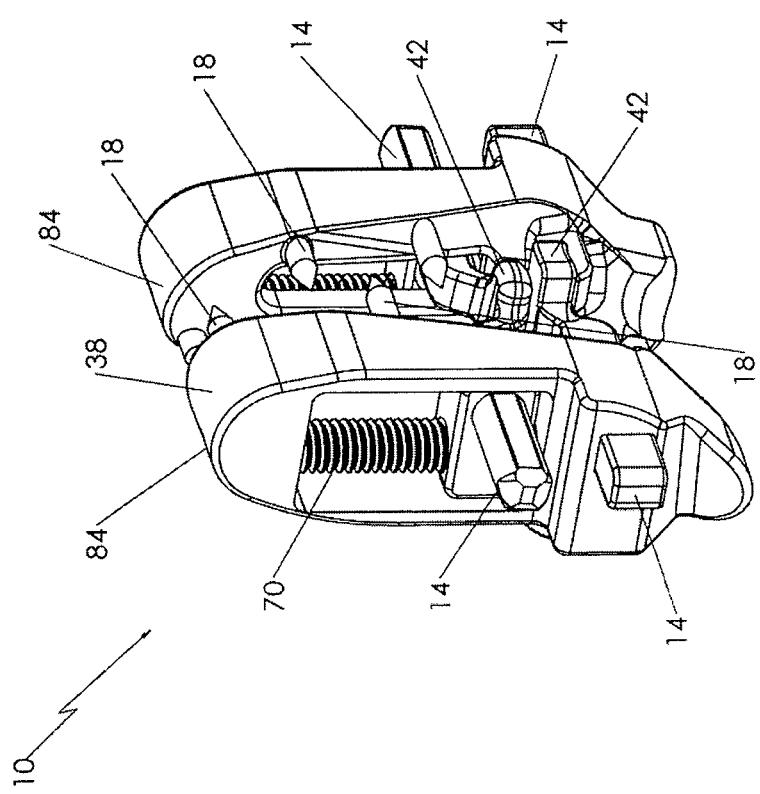
FIG. 13 shows a posterior perspective view of the fourth exemplary embodiment of the bi-dimensionally adjustable spinous process spacer device shown in FIG. 12.
Figure 15:
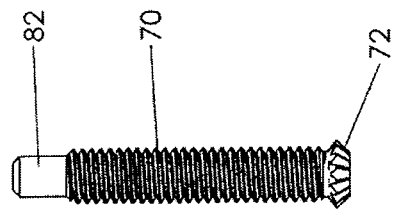
FIG. 15 shows the rotating vertically oriented gear for adjusting the distance between transverse members positioned between the spinous processes of adjacent vertebra of the fourth exemplary embodiment shown in FIG. 12.
Figure 14:
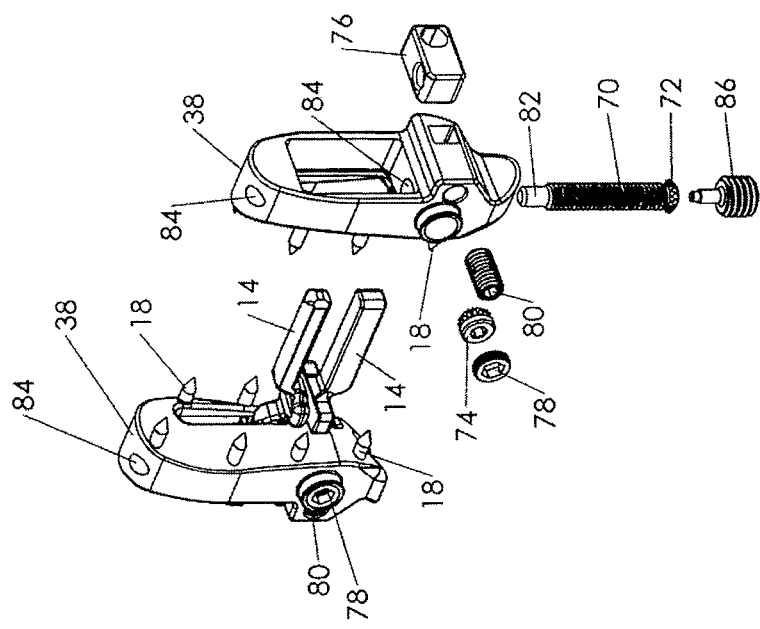
FIG. 14 shows an exploded view of the fourth exemplary embodiment of the bi-dimensionally adjustable spinous process spacer device shown in FIG. 12.

A fourth exemplary embodiment of the device 10 as shown in FIGS. 12-15 also has many similar elements to the earlier described exemplary embodiments that provide the basic function of the device 10, which is to allow adjustment of the device in two dimensions relative to the spine, that is longitudinal and lateral adjustment as described above. As best shown in FIG. 12, the side plates 38 are provided with surface contact structures, such as but not limited to spikes 18, for improved security of the contact to the lateral surface of the spinous process. As shown in FIGS. 13-15, the longitudinal adjustment of the transverse members 14 is accomplished by turning an elongated, vertically orient gear actuator 70 having an integral bevel gear element 72 at its inferior end. A gear drive actuator 74 terminating in a bevel gear complementary to the bevel gear element 72 of the elongated gear 70 when turned interacts with and causes the elongated gear 70 to rotate about its pivot base 86 at the base of the guide/gear box 76 upon which the elongated gear 70 can freely pivot. This interaction, depending upon the direction of rotation causes the guide/gear box to move upward or downward within the side plate 38. In doing so, the side plate 38 carries the transverse member along to the selected position in the side plate 38. It can then be locked into the selected position by the locking screw 78. When the lateral plate 38 is adjusted laterally relative to the transverse member such that gripping contact augmented by the surface contact structures such as spikes is achieved, the lateral set screw 80 can be secured into the lateral plate to hold the transverse member 14 in its selected lateral orientation to the spinous process.

Figure 16:
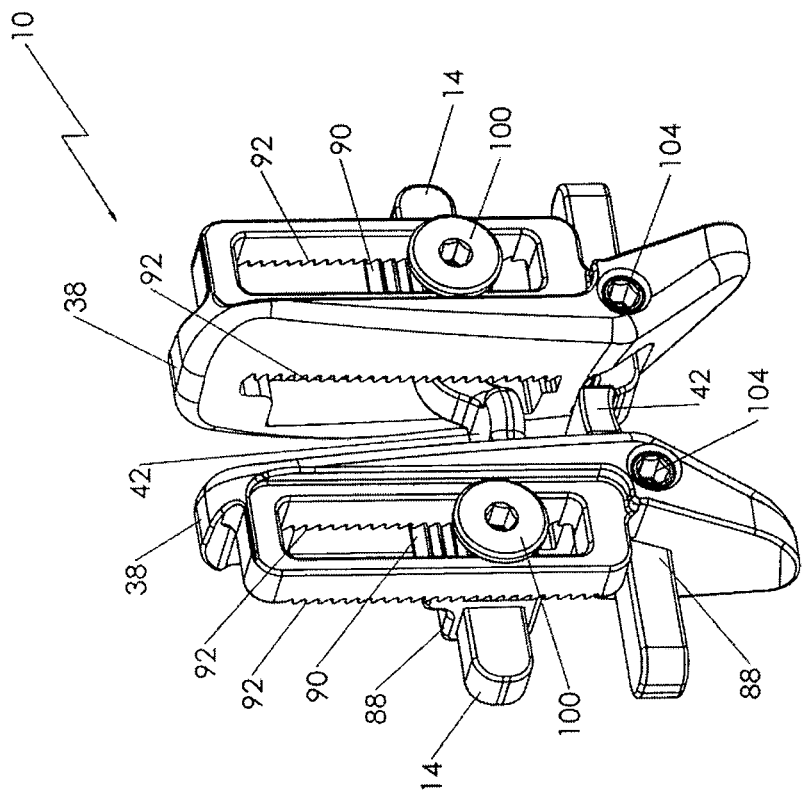
FIG. 16 shows a frontal perspective view of a fifth exemplary embodiment of the bi-dimensionally adjustable spinous process spacer device having a fitted posterior ratchet locking device to secure the device in a selected spatial relationship between the spinous processes of two adjacent vertebrae and using set screws to secure the device in a selected position against the lateral surface of the spinous process.
Figure 17:
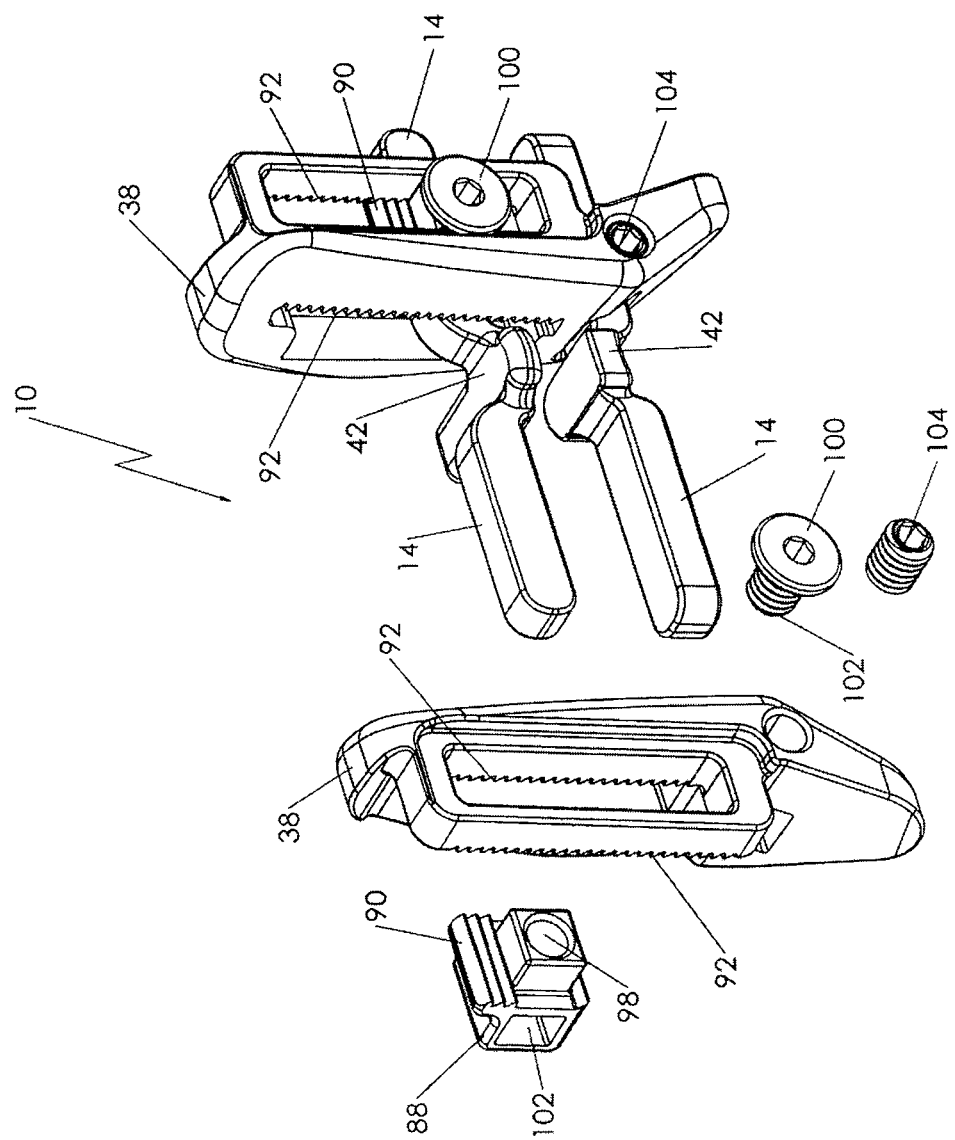
FIG. 17 shows an exploded view of the fifth exemplary embodiment of the bi-dimensionally adjustable spinous process spacer device of FIG. 16 having a fitted posterior ratchet locking device.
Figure 18:
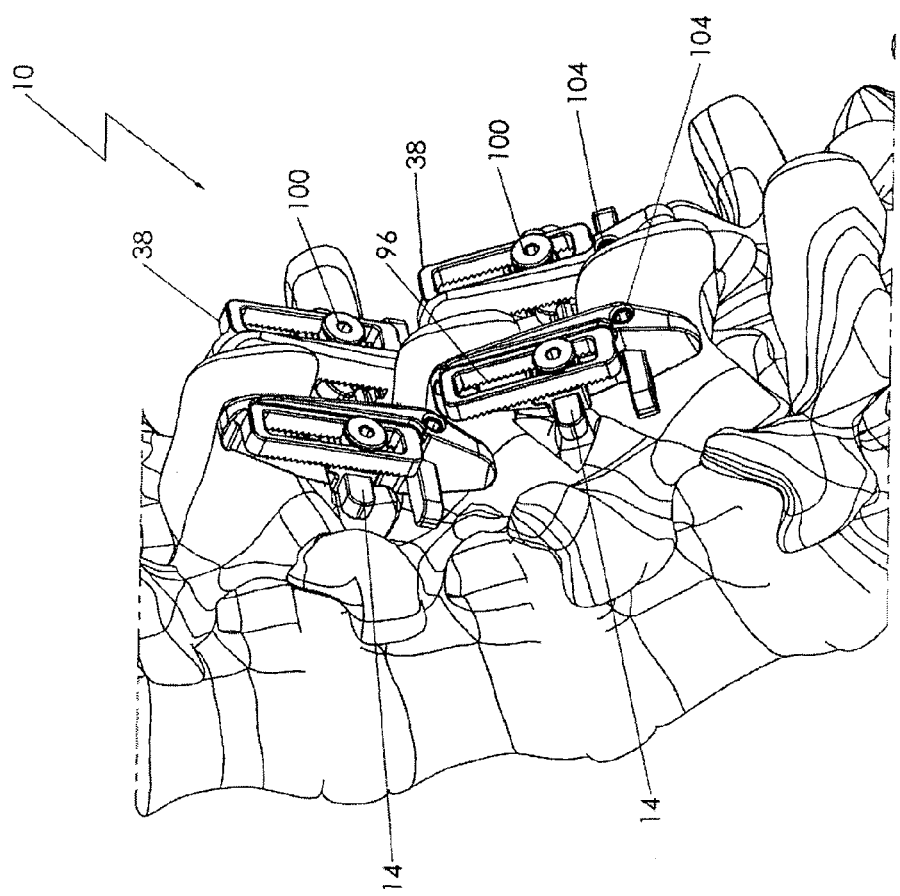
FIG. 18 shows two devices of the fifth exemplary embodiment of the bi-dimensionally adjustable spinous process spacer device of FIG. 16 having a fitted posterior ratchet locking device in position between adjacent vertebrae, holding the adjacent spinous processes in a fixed spatial relationship one to the other and having the device securely abutted against the lateral surfaces of the respective spinous processes.

A fifth exemplary embodiment of the device 10 as shown in FIGS. 16-18 is, as other embodiments capable of being adjusted longitudinally so as to set and hold the relative position of two adjacent spinous processes while also permitting adjustment of the transverse members 14 relative to the side plates 38. In this fifth exemplary embodiment of the device 10, the transverse members 14 pass through transverse member carriers 88 having forward facing ratchet teeth 90 or a similarly configured gripping surface that is complementary to rearward facing ratchet teeth 92 along the contact surface of the front wings 94 of the side plates 38. Define through the front wings 94 of the side plates 38 is the carrier access slots 96 through which a carrier locking element 100 can partially extend and make threaded contact with the locking element receptacle 98 on the transverse member carrier 88. When the carrier 88 is adjusted upward or downward along the longitudinal axis of the side plate 38 a selected position can be locked into place by tightening the carrier locking element 100 into the carrier locking element receptacle 98. As the locking element 100 is tightened it forces the forward facing ratchet teeth 90 of the carrier 88 into a locked engagement with the rearward facing ratchet teeth 92 of the front wing of the side plate 94. This locking arrangement is best shown in FIG. 16. Full insertion of the locking element 100 into the locking element receptacle 98 of the transverse member carrier 88 permits locking contact of the distal end 102 of the locking element 110 against the transverse member 14, which adjustable passes laterally through the transverse member carrier portal 102 of the carrier 88. Thus, when the device 10 is selectively positioned in both of the adjustable dimensions, longitudinally and laterally, the locking element 100 can be set to completely secure the device 10. A set screw 104, as with other exemplary embodiments of the device 10 can be used to lock the lower lateral-only adjustment transverse member 14.

Figure 19:
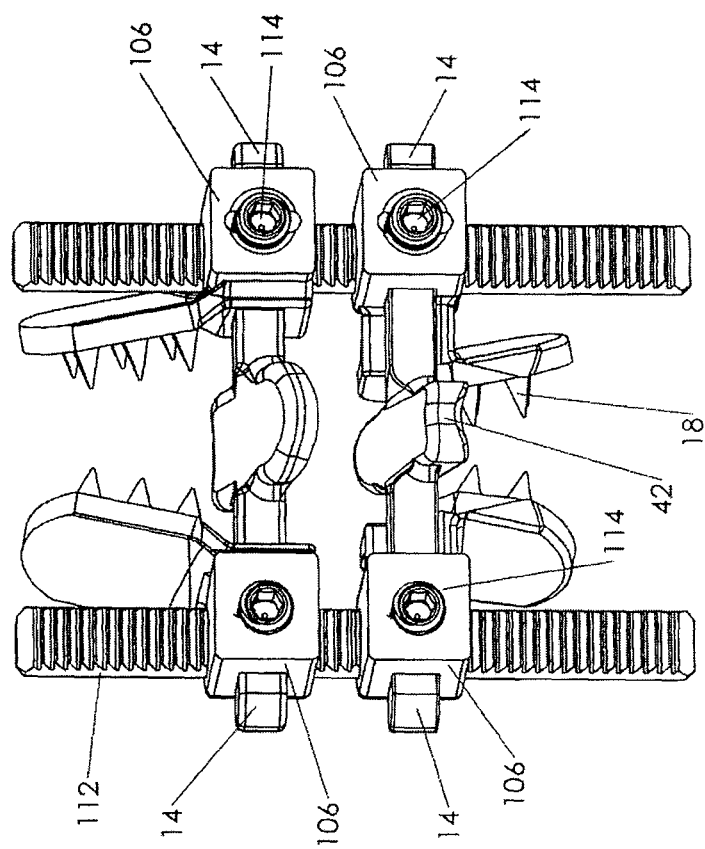
FIG. 19 shows a sixth exemplary embodiment of the bi-dimensionally adjustable spinous process spacer device with two adjacent transverse members mounted on substantially parallel elongated members, the elongated members having a plurality of gripping devices such as, for example, a toothed or ratcheted surface and being securable to the transverse members at selected positions by set screw locking blocks, the locking blocks also including spinous process lateral surface contact security elements such as, for example, inwardly directed spikes.
Figure 20:
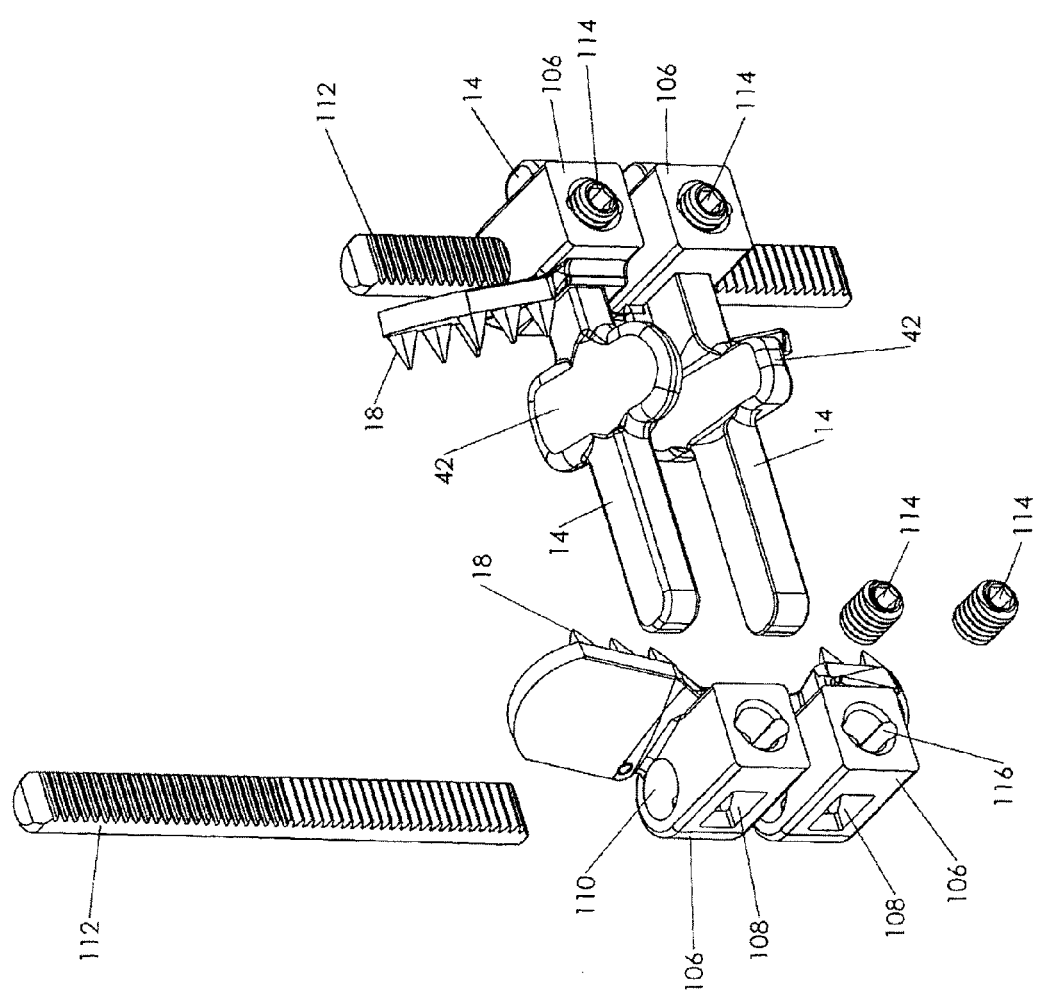
FIG. 20 shows an exploded view of the sixth exemplary embodiment of the bi-dimensionally adjustable spinous process spacer device shown in FIG. 19.
Figure 21:
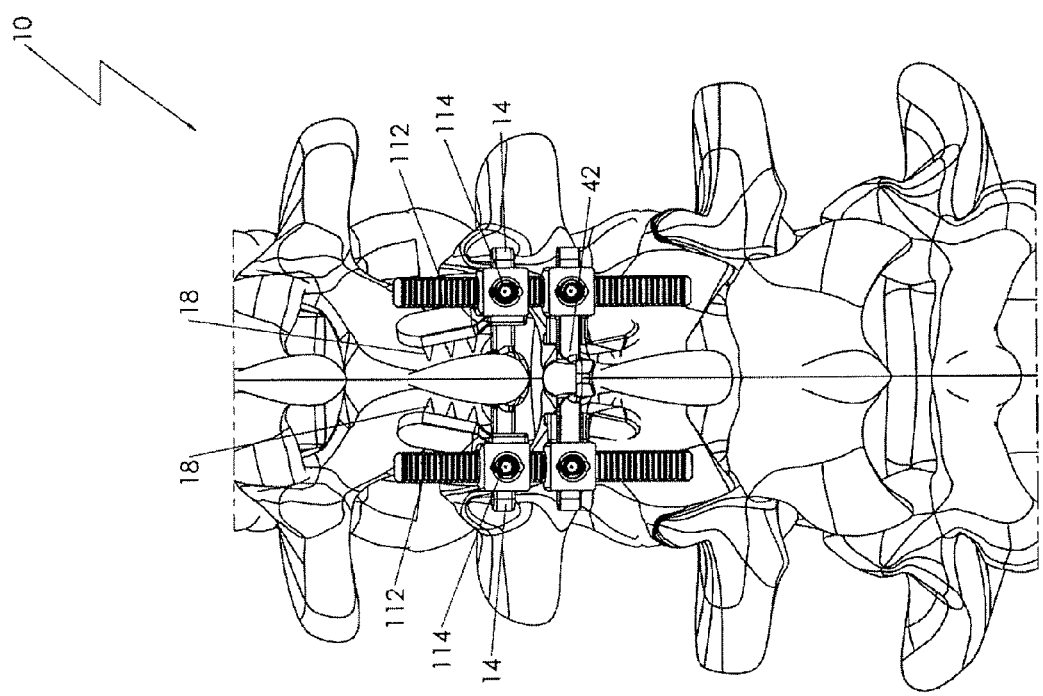
FIG. 21 shows two devices of the sixth exemplary embodiment of the bi-dimensionally adjustable spinous process spacer device of FIG. 19 positioned on adjacent vertebrae, the caudally position device being adjusted inwardly so as to bring the spinous process contact security elements into contact with the lateral surfaces of the spinous process and the superior positioned device not yet fully adjusted inwardly to cause contact between the contact security elements and the lateral surface of the spinous process of the superior vertebra.
Figure 25A:
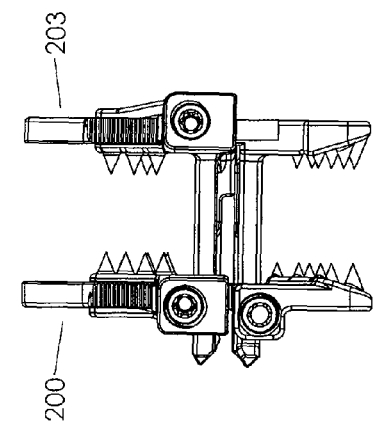
FIGS. 25A-25D show various views of the device.
Figure 25B:
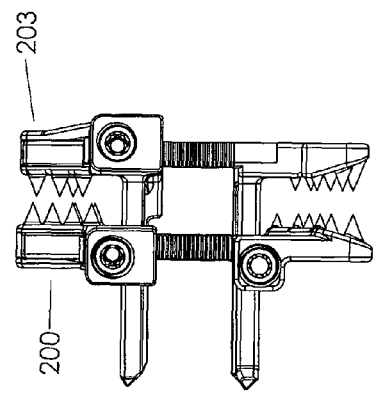
Figure 25C:
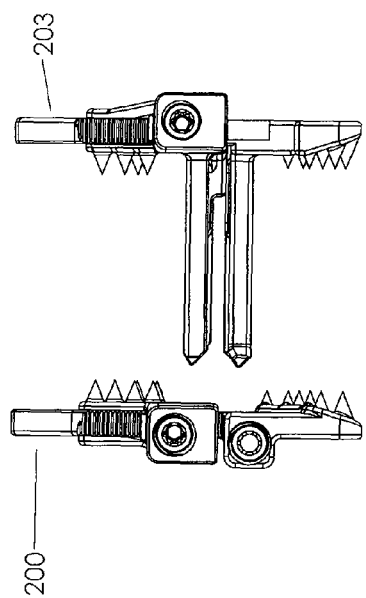
Figure 25D:
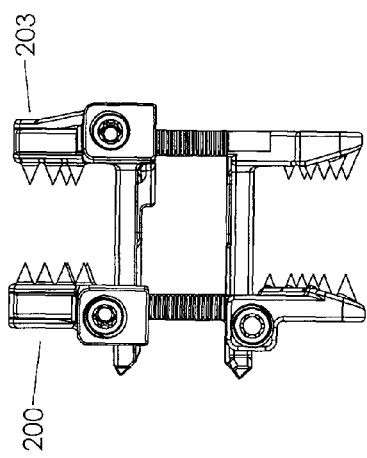

A sixth exemplary embodiment of the device 10 as shown in FIGS. 19-21 is also capable of being adjusted longitudinally and laterally as described for the other exemplary embodiments. In this sixth exemplary embodiment of the device 10, the transverse members 14 pass through transverse member carrier blocks 106, which are configured to allow adjustable passage of the transverse members through transverse member slots 108. Longitudinal elongated legs 112 having forward facing surface contact structures such as ratchet teeth are sized and configured to pass through a vertically oriented elongated leg receiving portals 110, the lumens of which intersect with the lumens of the transverse member slots 108 as shown in FIG. 20. When the longitudinal and lateral adjustment of the transverse members 14 and the elongated legs 112 are selectively positioned, the device set screws 114 can be securely set in the set screw receptacles 116 to fully lock the device 10. Also included in this sixth exemplary embodiment of the device 10 are spinous process engagement wings 116 extending inwardly from the carrier blocks 106. The engagement wings 116 can be provided with surface contact members such as spikes 18 or the like.

A seventh exemplary embodiment of the device 10 as shown in FIGS. 22A-25D is also capable of being adjusted longitudinally and laterally as described for the other exemplary embodiments. In this seventh exemplary embodiment of the device 10, the spinal device 10 comprises a first longitudinal member 200 having a first or cephalad end 201 and a second or caudal end 202, and a second longitudinal member 203 having a first or cephalad end 201 and a second or caudal end 202. A first or cephalad transverse member 12 and a second or caudal transverse member 14 adjust the distance between the first and second longitudinal members 200, 203 on a longitudinal and a lateral plane. The first 200 and second 203 longitudinal members are held in an approximately parallel orientation one to the other and positioned between spinous processes of two adjacent vertebrae.

The first longitudinal member 200 comprises an outer or distal wall 300, an inner or proximal wall 301, the walls been joined via a first and second side wall 302, 303, a through portal 230 and a locking mechanism. The first longitudinal member is shaped in a generally oblong shape having diametrically opposing sloping side walls 304, 305. The first longitudinal member 200 and the second longitudinal member 203 comprise a ratchet surface 221 for adjustably moving each of the spinous process pads 204 longitudinally.

The second longitudinal member 203 is shaped and sized to complement the first longitudinal member 200. Accordingly, the second longitudinal member 203 comprises an outer or distal wall 306, an inner or proximal wall 307, the walls been joined via a first and second side wall 308, 309, and a transverse member 14 connected to the inner or proximal side wall 307. The second longitudinal member 203 is shaped in a generally oblong shape having diametrically opposing sloping side walls 310, 311. The first longitudinal member 200 and the second longitudinal member 203 comprise a ratchet surface 221 on their respective side walls 302, 311 for adjustably moving each of the spinous process pads 204, 222 longitudinally.

The first and second longitudinal members 200, 203 comprise bone plates 313 at the caudal end of the longitudinal members 200, 203 having anchoring structures 213 disposed thereon facing the spinal process for anchoring the device 10. In some embodiments, the bone plates 313 at the caudal or distal 202 end of the first and/or second longitudinal members 200, 203 comprise an angled surface. In these embodiments, the surface slopes away from the bone whereby the surface anchor/gripping structure size 213 proportionally increases to provide contact between the bone and the anchoring structures 213. In other embodiments, the bone plates 313 slope inwards towards the bone, or are planar. The bone plate 313 of the second longitudinal member further comprises a lip 312.

A first spinous process pad 204 is dimensioned to slidably fit over at least the top or cephalad 201 portion of the first 200 longitudinal member. The spinous process pad 204 allows for an increase in longitudinal motion and/or anchoring. The spinous process pad 204 comprises a first plate 205 and a second plate 206 in an approximately parallel orientation to one another, an aperture or through portal 207 which is dimensioned to receive the first transverse member 12. The second plate 206 comprises one or more surface anchoring structures 213 for anchoring to a spinous process. The spinous process pad 204 comprises a position locking mechanism 211 which has an integrated threaded aperture 208 for receipt of a set screw 209 and locking plate 210.

A second spinous pad 222 is dimensioned to slidably fit over at least the top or cephalad 201 portion of the second 203 longitudinal member to allow longitudinal adjustment of the first and second longitudinal members 200, 203 relative to the transverse members 12, 14. The spinous process pad 222 allows for an increase in longitudinal motion and/or anchoring. The spinous process pad 222 comprises a first plate 205 and a second plate 206 in an approximately parallel orientation to one another, a first transverse member 12 connected to the second plate 206 and aligned with the aperture or through portal 207 of the first spinous process pad 204. The second plate 206 comprises one or more surface anchoring structures 213 for anchoring to a spinous process. The spinous process pad 222 comprises a position locking mechanism which has a locking plate 210, a set screw 209 and a carrier plate 223. The carrier plate 223 comprises an integrated threaded aperture 208 for receipt of the set screw 209 and an expansion tool interface 224. The transverse members 12, 14 engage the first longitudinal member 200 via the through portals 207 which receive the upper and lower transverse members 12, 14.

The first and second transverse members 12, 14 are adjustably connected to the first or second longitudinal member 200, 203 and each of the transverse members 12, 14 align so as to position the first and second longitudinal members 200, 203 on either side of the spinal process. The first longitudinal member 200 comprises a threaded set screw receiving member 212 which is positioned and integrated into the side of the distal or caudal end 202 of the first longitudinal member 200 for adjusting and locking the lower transverse member 14 into position. The lower or caudally positioned transverse member 14 comprises a depression 215 running approximately along the length of the center of the lower transverse member 14 and an aperture 216 is disposed proximally to the inner side 217 of the second longitudinal member 203. The lower or caudal transverse member 14 further comprises an approximately U-shaped hook-like protrusion or plate retainer 218 having an approximately curved outer side for slidably engaging the side of the first longitudinal member. The upper or cephalad transverse member 12 comprises an approximately U-shaped hook-like protrusion or plate retainer 219 for slidably engaging the side of the first longitudinal member. The first 12 and/or second 14 (caudal 12 and/or cephalad 14) transverse members optionally comprise an inter-laminar tongue or protrusion 220 for further stabilization of the device.

The first and second spinal process pads 204, 222 comprise a collet lock mechanism 211 comprising an interlock plate 210 and set screw 209 for adjustably securing the positioning of the upper or cephalad transverse member 12 and for longitudinal adjustment of the spinous process pads 204, 222 in relation to the longitudinal members 200, 203. The interlock plate 210 comprises a ratchet surface 213 that is inversely shaped with respect to the ratchet surface 308 of the first and second longitudinal members 200, 203 for longitudinal adjustment of the transverse members 12, 14.

The cephalad transverse member 12 is locked into position via the interlock mechanism 211 of the cephalad spinous process pad 204. The caudal transverse member 14 is locked into position by tightening the set screw 209 which is received into the threaded aperture 208. The position locking mechanisms are capable of securely holding each of the first 12 and second 14 transverse members in a selected position relative to the first 200 and second 203 longitudinal members and the respective adjacent spinous processes after the first 12 and second 14 transverse members have been selectively adjusted both laterally and longitudinally relative to the longitudinal members 201, 203 and the respective adjacent spinous processes. The collet lock mechanism 211 of the spinous process pad 222 further comprises an expansion tool interface 220 for longitudinal and/or lateral adjustment of the upper or cephalad transverse member 12.

The features of the device 10 can be embodied in various configurations and combinations, not all of which have been recited in the examples discussed herein. The components of the device 10 can be manufactured in various sizes of varying relative dimensions and geometry to conform to the natural shape of the spinous process. Furthermore, it is also within the understanding of the inventors that the device can be manufactured of any known materials having the necessary strength and resiliency to meet the operational requirements of the invention. Such variations in the device 10 can be used as necessary to improve the function of the device for the needs of a particular patient.

The device 10 can be manufactured as components by methods known in the art, to include, for example, molding, casting, forming or extruding, and machining processes. The components can be manufactured having a variety of different dimensions so as to provide components that can be selected by the surgeon as being best suited to the anatomical size and conformation of individual patient's vertebral structure. Non-limiting examples of materials that may be used at least in part for components of the device 10 include, for example, implant grade metallic materials, such as titanium, titanium alloy, cobalt-chromium alloys, stainless steel, and the like. Additionally, the structures of the device 10 can be manufactured wholly or in part using non-metallic materials such as, for example, carbon fiber composites, PEEK, PEKK, or other suitable non-metallic materials.

It is also within the concept of the present invention to provide a kit, which can include all components of the inventive device as well as necessary instruments and tools to facilitate the surgical procedure and additional instruments and/or implants or components which can be employed as deemed necessary by the surgeon. Such a kit can be provided with sterile packaging to facilitate opening and immediate use in an operating room.

For each of the exemplary embodiments of the device 10 disclosed herein, the method of use of the device 10 includes providing a bi-dimensionally adjustable spinous process spacer device capable of securely maintaining a selected distance between the spinous processes of two or more adjacent vertebrae and also allowing for lateral positioning of elements of the device 10 so as to make secure contact with the lateral surfaces of the spinous process of the vertebrae to which the device is attached, adjusting the device so as to obtain the desired spacing between the two or more adjacent spinous processes of the vertebrae of interest and selectively adjusting the lateral position of the elongated legs of the device relative to the spinous processes, locking the device securely into the selected position.

Each of the embodiments described above are provided for illustrative purposes only and it is within the concept of the present invention to include modifications and varying configurations without departing from the scope of the invention that is limited only by the claims included herewith.

What is claimed is:

1. A spinal device comprising:
a first longitudinal member having a first end and a second end with a first ratchet surface formed along a length therebetween,
a second longitudinal member having a first end and a second end with a second ratchet surface formed along a length therebetween,
a first and second transverse member,
a first spinous process pad having an inverse ratchet surface dimensioned to slidably fit over a top portion of said first longitudinal member for longitudinal adjustment with said first ratchet surface, said spinous process pad comprising a first plate and a second plate in an approximately parallel orientation to one another, an aperture dimensioned to receive said first transverse member, and a threaded aperture for receipt of a set screw and a locking plate,
a second spinous process pad having an inverse ratchet surface dimensioned to slidably fit over a top portion of said second longitudinal member for longitudinal adjustment with said second ratchet surface, said spinous process pad comprising a proximal plate and a distal plate in an approximately parallel orientation to one another wherein said proximal plate is connected to said first transverse member, a threaded aperture for receipt of a set screw, and a locking plate,
a position locking mechanism capable of securely holding each of said first and second transverse members in a selected position relative to said first and second longitudinal members and respective adjacent spinous processes after said first and second transverse members have been selectively adjusted both laterally and longitudinally relative to said longitudinal members and the respective adjacent spinous processes.

2. The spinal device of claim 1, wherein said first longitudinal member comprises a through portal which aligns with said second transverse member connected to said second longitudinal member in a direction generally aligned with the longitudinal axis of the spine, said through portal being configured to permit both longitudinal and lateral adjustment of said longitudinal members relative to said transverse member.

3. The spinal device of claim 2, wherein said second longitudinal member is connected to said second transverse member on an inner or proximal sidewall and aligned with said through portal of said first longitudinal member.

4. The spinal device of claim 1, wherein said first longitudinal member includes a threaded set screw receiving member positioned and integrated into said first longitudinal member for locking said second transverse member into position.

5. The spinal device of claim 1, wherein said first and second transverse members are capable of being adjustably connected so each of said transverse members align and position said first and second longitudinal members on either side of the spinal process.

6. The spinal device of claim 1, wherein said second transverse member comprises a depression approximately along the length of the center of said transverse member and an aperture disposed proximally to said second longitudinal member.

7. The spinal device of claim 1, wherein said second transverse member further comprises an approximately U-shaped hook-like protrusion having an approximately curved outer side.

8. The spinal device of claim 1, wherein said first transverse member comprises an approximately U-shaped hook-like protrusion for slidably engaging an outer side of said through portal of said first longitudinal member.

9. The spinal device of claim 1, wherein said first and second transverse members being adjustably connected to said first or second longitudinal members so as to be positioned between adjacent spinous processes of vertebrae.

10. The spinal device of claim 1, wherein said first and second longitudinal members comprise one or more surface anchor structures disposed on at least a portion of a lower, inner surface facing said spinous process of said first and second longitudinal members.

11. The spinal device of claim 10, wherein said first and/or second transverse members further comprise a plate retainer.

12. The spinal device of claim 1, wherein said first and second spinal process pads comprise a collet lock mechanism comprising an interlock plate and set screw for adjustably securing the positioning of said first transverse member.

13. The spinal device of claim 12, wherein said collet lock mechanism of said second spinal process pad further comprises an expansion tool interface for longitudinal and/or lateral adjustment of said first transverse member.

14. The spinal device of claim 1, wherein an end of said first and/or second longitudinal members comprise an angled surface, each said angled surface sloping away from an inner surface of each said first and/or second longitudinal members.

15. The spinal device of claim 1, wherein said transverse members include an inter laminar tongue.

\* \* \* \* \*